United States Patent
Zhang et al.

(10) Patent No.: US 11,465,186 B2
(45) Date of Patent: Oct. 11, 2022

(54) MICROWAVE PLASMA GASIFICATION AND RECYCLE INTEGRATED SYSTEM FOR DOMESTIC GARBAGE

(71) Applicant: TSINGHUA UNIVERSITY, Beijing (CN)

(72) Inventors: Guixin Zhang, Beijing (CN); Cheng Liu, Beijing (CN); Hong Xie, Beijing (CN); Lei Deng, Beijing (CN)

(73) Assignee: TSINGHUA UNIVERSITY, Beijing (CN)

(*) Notice: Subject to any disclaimer, the term of this patent is extended or adjusted under 35 U.S.C. 154(b) by 430 days.

(21) Appl. No.: 16/652,679

(22) PCT Filed: Jul. 5, 2018

(86) PCT No.: PCT/CN2018/094713
§ 371 (c)(1),
(2) Date: Apr. 1, 2020

(87) PCT Pub. No.: WO2019/100728
PCT Pub. Date: May 31, 2019

(65) Prior Publication Data
US 2020/0238350 A1    Jul. 30, 2020

(30) Foreign Application Priority Data
Nov. 21, 2017   (CN) .......................... 201711167906.2

(51) Int. Cl.
*B09B 3/00*    (2022.01)
*B09B 3/40*    (2022.01)
(Continued)

(52) U.S. Cl.
CPC ...... *B09B 3/40* (2022.01); *A61L 2/18* (2013.01); *A61L 11/00* (2013.01); *B65F 3/001* (2013.01);
(Continued)

(58) Field of Classification Search
CPC ................................... B09B 3/40; B09B 5/00
(Continued)

(56) References Cited

U.S. PATENT DOCUMENTS
5,173,257 A    12/1992  Pearson

FOREIGN PATENT DOCUMENTS
CN    105642645    6/2016
CN    106429121    2/2017
(Continued)

OTHER PUBLICATIONS

"International Search Report (Form PCT/ISA/210) of PCT/CN2018/094713", dated Oct. 11, 2018, with English translation thereof, pp. 1-4.

*Primary Examiner* — Gregory E Webb
(74) *Attorney, Agent, or Firm* — JCIP Global Inc.

(57) ABSTRACT

A microwave plasma gasification and recycle integrated system for domestic garbage. The system is fixed in a garbage truck compartment with a garbage inlet, and includes a closed chain-plate type feeder, a shredding machine, and a closed magnetic separator which are connected in sequence. The magnetic separator is further separately connected to a microwave plasma gasification furnace and a metal recycle tank. The microwave plasma gasification furnace is further separately connected to a stink processor, a plastic residue recycle tank, an integrated sewage treatment device, and a residue smashing machine. The stink processor is connected to a gas recycle tank. Both the residue smashing machine and the integrated sewage treatment device are connected to an aerobic fermentation tank. The aerobic fermentation tank is connected to a decomposed material recycle tank by means of a decomposed material forming and screening machine.

7 Claims, 2 Drawing Sheets

(51) Int. Cl.
  *A61L 2/18* (2006.01)
  *A61L 11/00* (2006.01)
  *B65F 3/00* (2006.01)
  *B65F 3/14* (2006.01)
(52) U.S. Cl.
  CPC ........ *B65F 3/143* (2013.01); *B65F 2003/006* (2013.01)
(58) Field of Classification Search
  USPC .......................................................... 422/186
  See application file for complete search history.

(56) References Cited

FOREIGN PATENT DOCUMENTS

| | | | |
|---|---|---|---|
| CN | 107824602 | 3/2018 | |
| CN | 207655631 | 7/2018 | |
| KR | 101669004 B1 * | 10/2016 | ................ C10J 3/20 |
| WO | 2005120713 | 12/2005 | |

\* cited by examiner

MICROWAVE PLASMA GASIFICATION AND RECYCLE INTEGRATED SYSTEM FOR DOMESTIC GARBAGE

BACKGROUND

Technical Field

The present application relates to the field of garbage disposal by using microwave plasma, and in particular, to an integrated microwave plasma gasification and recycling system for domestic garbage.

Description of Related Art

With the increase of economic strength and technical reserve in China, various domestic garbage disposal technologies have been studied and applied to different degrees and in different areas throughout the country, and a variety of disposal facilities such as modern landfill sites, mechanized composting plants, and incineration plants have been built in many regions.

At present, a single disposal mode is mainly adopted in disposing domestic garbage in China, that is, using sanitary landfill as the main manner and garbage incineration and composting as the auxiliary manner. However, direct landfill of garbage will cause a waste of resources since the garbage produced in our country have complex components and higher amount of organisms; and the obtained composts has relatively low fertilizer efficiency and hardly produce economic benefits since too much litters are contained therein. Incineration cannot achieve the transfer and reuse of resources and, instead, produce bad smells that are difficult to deal with and contaminate the atmosphere.

Therefore, a single disposal mode cannot meet the requirements of harmlessness, reduction and resource utilization in disposing domestic garbage that are increasing in amount and increasingly complex in components. For example, Chinese Patent Application No. 201611090647.3 titled Domestic Garbage Truck Having Crushing, Wind Sorting and Compressing Functions, and Chinese Patent Application No. 201620134349.9 titled A Domestic Garbage Crushing and Wind Sorting Device provided only a vehicle arrangement for recycling and sorting garbage, which, however, cannot achieve immediate and all-time disposal of domestic garbage. For another example, the Chinese Patent Application No. 201611090647.3 titled Domestic Garbage Crushing and Wind Sorting Device merely disclosed a conceptual device for crushing and compressing garbage, but did not mention subsequent process of reduction and harmlessness of garbage.

SUMMARY

Regarding the defects present in the prior arts, the present application provides an integrated microwave plasma gasification and recycling system for domestic garbage, which can effectively address the above-mentioned problems.

The present application provides the following technical solutions.

An integrated microwave plasma gasification and recycling system for domestic garbage, which is fixed in the carriage of a garbage truck having a garbage inlet, and comprises a closed chain-plate feeder, a shredder, a closed magnetic separator, a microwave plasma gasifier, an odor treatment device, a remnant pulverizer, an integrated sewage treatment equipment, a decomposed material forming and screening machine, an aerobic fermentation tank, a decomposed material recovery tank, a plastic slag recovery tank, a metal recovery tank, and a gas recovery tank. The closed magnetic separator has a metal material discharge port and a non-metal garbage discharge port, the microwave plasma gasifier has a feed port, a solid remnant recovery port for recovering organic garbage, a plastic slag recovery port, a leachate recovery port and an exhaust port, and the aerobic fermentation tank has a solid garbage feed port, a liquid waste feed port and a discharge port.

The garbage inlet of the carriage of the garbage truck is connected with a feed port of the closed chain-plate feeder, and original domestic garbage is charged into the closed chain-plate feeder via the feed port of the closed chain-plate feeder. A discharge port of the closed chain-plate feeder is connected with a feed port of the shredder. A discharge port of the shredder is connected with the feed port of the closed magnetic separator. The non-metal garbage discharge port of the closed magnetic separator is connected with the feed port of the microwave plasma gasifier, and the metal material discharge port of the closed magnetic separator is connected with the metal recovery tank. The solid remnant recovery port, the plastic slag recovery port, the leachate recovery port and the exhaust port of the microwave plasma gasifier are connected with a feed port of the remnant pulverizer, the plastic slag recovery tank, a feed port of the integrated sewage treatment equipment, and the gas inlet of the odor treatment device, respectively, and the gas outlet of the odor treatment device is connected with the gas recovery tank. A discharge port of the remnant pulverizer and a discharge port of the integrated sewage treatment equipment are connected with the solid garbage feed port and liquid waste feed port of the aerobic fermentation tank, respectively. The discharge port of the aerobic fermentation tank is connected with a feed port of the decomposed material forming and screening machine, and a discharge port of the decomposed material forming and screening machine is connected with the decomposed material recovery tank.

Preferably, the microwave plasma gasifier comprises a housing and a microwave plasma torch generator, a non-metal garbage conveyor with sieve pores, a reaction tank, a sewage extrusion separator, and a hopper respectively fixed within the housing via brackets. The exhaust port of the microwave plasma gasifier is provided at a top portion of the housing, the plastic recovery port and the leachate recovery port of the microwave plasma gasifier are respectively provided at a bottom portion of the housing, and the feed port and the solid remnant recovery port of the microwave plasma gasifier are provided at an upper part of two opposite side walls of the housing. The reaction tank is located in a left part of the microwave plasma gasifier, with a top part and a bottom part of the reaction tank being connected with the exhaust port and the leachate recovery port of the microwave plasma gasifier, respectively. The microwave plasma torch generator is disposed close to an upper right part of the reaction tank, and a microwave plasma torch emission end of the microwave plasma torch generator is located within the reaction tank. The non-metal garbage conveyor is located below the microwave plasma torch emission end and extends through a middle part of the reaction tank, with one end thereof disposed closely under the solid remnant recovery port and the other end thereof fixed on the side wall of the housing opposite to the solid remnant recovery port. The sewage extrusion separator and the hopper are located above and under the non-metal garbage conveyor, respectively, and are both co-axially disposed at a right side of the reaction tank, with a feed port of the sewage extrusion separator being connected with the feed port of the microwave plasma gasifier and a bottom of the hopper being connected with the leachate recovery port of the microwave plasma gasifier.

Preferably, the microwave plasma torch generator comprises sequentially connected microwave generator, circulator and water load and microwave waveguide resonator. A non-metal microwave discharge tube used for emitting a microwave plasma torch is provided at a position where the microwave waveguide resonator has a maximum amplitude of microwave electric field, and the non-metal microwave discharge tube is perpendicular to an axis of the microwave waveguide resonator and has a lower end protruding out of the microwave waveguide resonator. A discharge wire is further fixed within the non-metal microwave discharge tube.

The integrated microwave plasma gasification and recycling system for domestic garbage provided by the present application has the following advantages.

By using a comprehended garbage disposal mode, the present application systematically combines a plurality of domestic garbage disposal equipment together to form a complete disposal system, improving the effect of domestic garbage disposal achieving the reuse of domestic garbage on the basis of harmless domestic garbage, and producing no secondary pollution to the environment.

By using a shredder, the present application is capable of uniformly breaking original garbage into a diameter size of 7-10 cm, greatly reducing the difficulties encountered in sequential treatments. This system divides the complex garbage disposal remnants into three classes via a microwave plasma gasifier and corresponding sequential treatment devices: non-metal solid remnant such as organic masses, which can be further treated and aerobically fermented in the aerobic fermentation tank to become half product of organic fertilizer, which can be conventionally processed to provide an organic fertilizer; plastics, some of which is gasified and most of which is molten to liquid state, sent to the liquid remnant recovery port where it condenses to solid plastic slag, and recovered in the plastic slag tank so that it can be further reused; and gaseous substances, generally carbon dioxide and water vapor, possibly containing some products of incomplete combustion, which are recovered to avoid atmosphere pollution and carbon discharge. Finally, after being treated by the present system, nearly most of the garbage in original domestic garbage can be effectively and harmlessly treated, producing significant effects in reduction and reuse of garbage.

Sealing treatments are adopted in all the equipment in the present application, and waste gases as produced are treated in the odor treatment device and exhausted after reaching discharge standards, guaranteeing a clean and odorless overall treatment environment and a good working environment for the workers.

The present application has the advantages of high reliability, fast disposal speed and high screening rate of domestic garbage, and free of hazards such as dusts, noise or the like.

DESCRIPTION OF THE EMBODIMENTS

The present application will be further described in detail below in connection with drawings and examples, for the purpose of better understanding the technical problems to be solved, technical solutions, and beneficial effects of the present application. It is to be understood that the particular embodiments described herein are merely provided for explaining the present application, and not intended to limit the present application.

Figure 1:
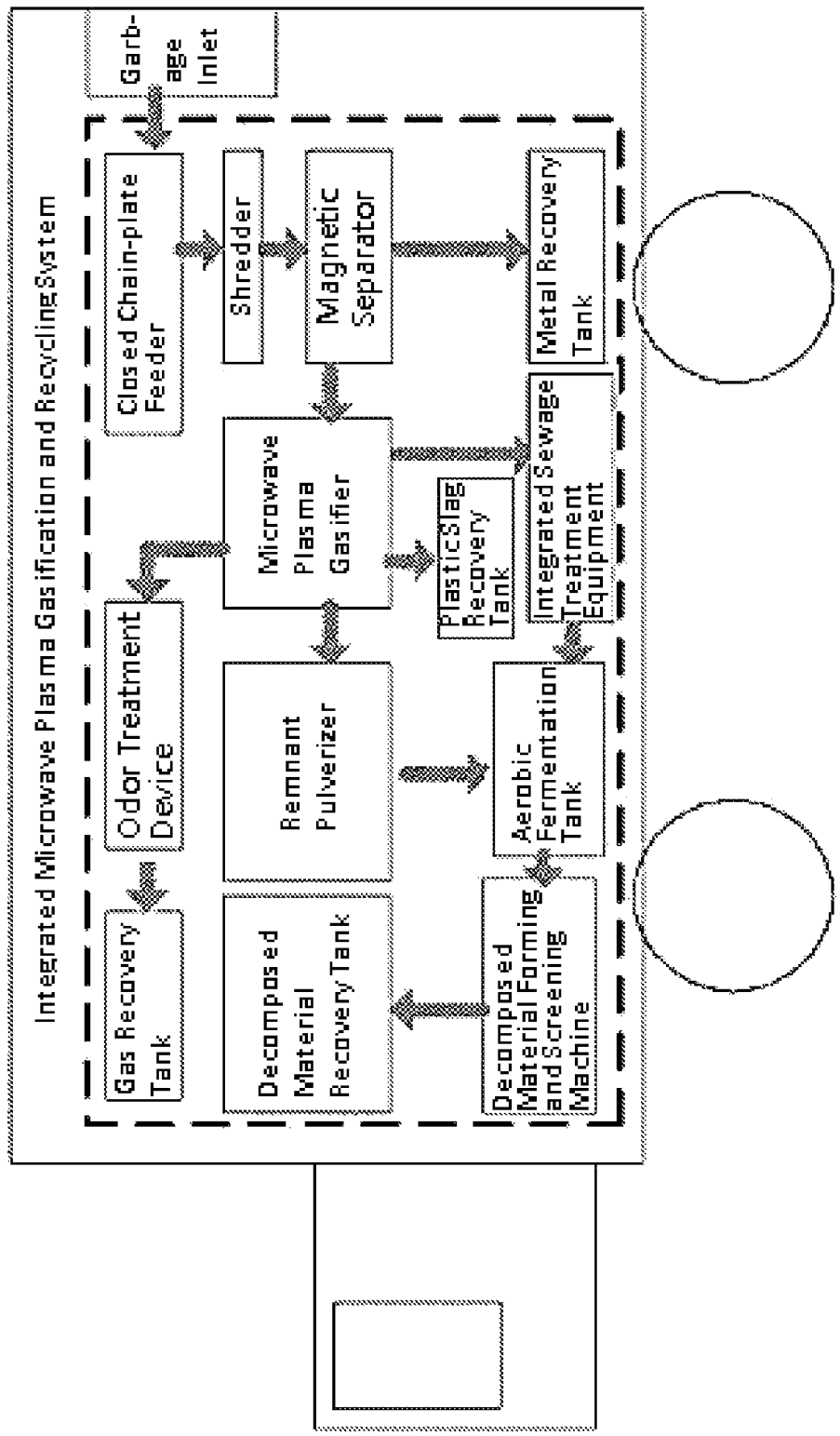
FIG. 1 is a schematic diagram of an overall structure of an embodiment according to the present application.

The present application provides an integrated microwave plasma gasification and recycling system for domestic garbage, which is fixed in the carriage of a garbage truck having a garbage inlet (having an overall structure shown in FIG. 1), and comprises a closed chain-plate feeder, a shredder (which is a double shaft pulverizer in this example, providing a post-pulverization garbage particle size of 7-10 cm), a closed magnetic separator, a microwave plasma gasifier, an odor treatment device, a remnant pulverizer, an integrated sewage treatment equipment, a decomposed material forming and screening machine, an aerobic fermentation tank, a decomposed material recovery tank, a plastic slag recovery tank, a metal recovery tank, and a gas recovery tank. The closed magnetic separator has a metal material discharge port and a non-metal garbage discharge port, the microwave plasma gasifier has a feed port, a solid remnant recovery port (for recovering organic garbage), a plastic slag recovery port, a leachate recovery port and an exhaust port, and the aerobic fermentation tank has a solid garbage feed port, a liquid waste feed port and a discharge port.

In particular, the garbage inlet of the carriage of the garbage truck is connected with a feed port of the closed chain-plate feeder, and original domestic garbage is charged into the closed chain-plate feeder via the feed port of the closed chain-plate feeder. A discharge port of the closed chain-plate feeder is connected with a feed port of the shredder. A discharge port of the shredder is connected with the feed port of the closed magnetic separator. The non-metal garbage discharge port of the closed magnetic separator is connected with the feed port of the microwave plasma gasifier, and the metal material discharge port of the closed magnetic separator is connected with the metal recovery tank. The solid remnant recovery port, the plastic slag recovery port, the leachate recovery port and the exhaust port of the microwave plasma gasifier are connected with a feed port of the remnant pulverizer, the plastic slag recovery tank, a feed port of the integrated sewage treatment equipment, and a gas inlet of the odor treatment device, respectively, and the gas outlet of the odor treatment device is connected with the gas recovery tank. A discharge port of the remnant pulverizer and a discharge port of the integrated sewage treatment equipment are connected with the solid garbage feed port and liquid waste feed port of the aerobic fermentation tank, respectively. The discharge port of the aerobic fermentation tank is connected with a feed port of the decomposed material forming and screening machine, and a discharge port of the decomposed material forming and screening machine is connected with the decomposed material recovery tank.

Figure 2:
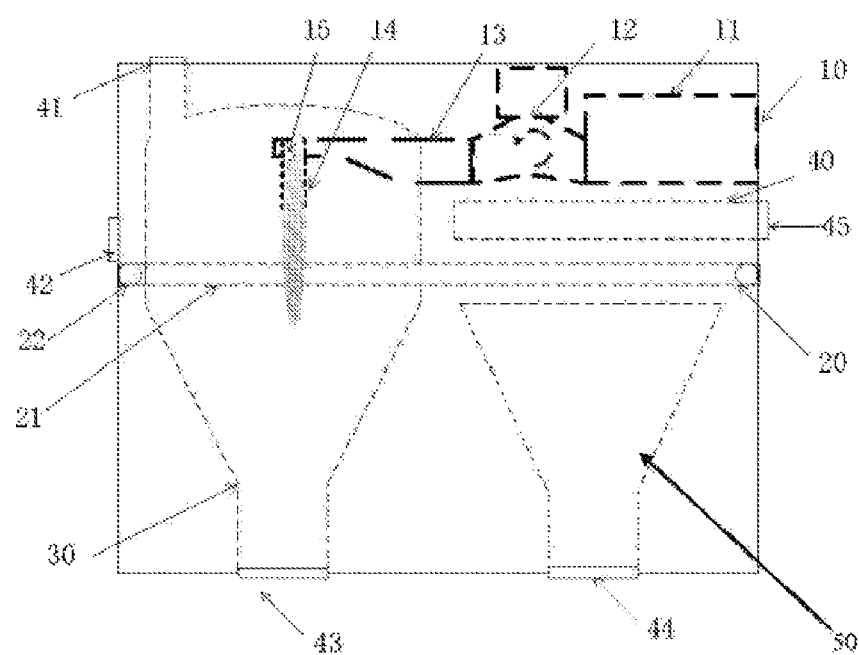
FIG. 2 is a schematic structural diagram of a microwave plasma gasifier according the present application.

Particular implementations and functions of various components of the integrated system according to the present invention are described as blow:

The microwave plasma gasifier has a structure shown in FIG. 2, comprising a housing and a microwave plasma torch generator 10, a non-metal garbage conveyor 20 with sieve pores, a reaction tank 30, a sewage extrusion separator 40, and a hopper 50 respectively fixed within the housing via brackets. The exhaust port 41 of the microwave plasma gasifier is provided at a top portion of the housing, the plastic recovery port 43 and the leachate recovery port 44 of the microwave plasma gasifier are respectively provided at the bottom of the housing, and the feed port 45 and the solid remnant recovery port 42 of the microwave plasma gasifier are provided at an upper part of two opposite side walls of the housing. In particular, the reaction tank 30 is located in a left part of the microwave plasma gasifier, with a top part and a bottom part of the reaction tank 30 being connected with the exhaust port 41 and the leachate recovery port 44 of the microwave plasma gasifier, respectively. The microwave plasma torch generator 10 is disposed close to an upper right part of the reaction tank 30, and a microwave plasma torch emission end of the microwave plasma torch generator is located within the reaction tank 30. The non-metal garbage conveyor 20 is located below the microwave plasma torch emission end and extends through a middle part of the reaction tank 30, with one end thereof disposed closely under the solid remnant recovery port 42 and the other end thereof fixed on the side wall of the housing opposite to the solid remnant recovery port 42. The sewage extrusion separator 40 and the hopper 50 are located above and under the non-metal garbage conveyor 20, respectively, and are both co-axially disposed at a right side of the reaction tank, with a feed port of the sewage extrusion separator 40 being connected with the feed port 45 of the microwave plasma gasifier and a bottom of the hopper 50 being connected with the leachate recovery port 44 of the microwave plasma gasifier.

The particular structure and function of various components of the microwave plasma gasifier are described as follow.

The microwave plasma torch generator 10 has a structure as shown in FIG. 2, comprising sequentially connected microwave generator 11, circulator and water load 12 and microwave waveguide resonator 13. In particular, the output end of the microwave generator 11 is connected with the input end of the circulator and water load 12, and the output end of the circulator and water load 12 is connected with the input end of the microwave waveguide resonator 13. A non-metal microwave discharge tube 14 used for emitting a microwave plasma torch is provided at a position where the microwave waveguide resonator 13 has a maximum amplitude of microwave electric field. The non-metal microwave discharge tube is perpendicular to an axis of the microwave waveguide resonator 13 and has a lower end protruding out of the microwave waveguide resonator 13. A discharge wire 15 is further fixed within the non-metal microwave discharge tube. In particular, the microwave generator 11 adopts conventional microwave generation devices such as a magnetron, a velocity-modulated tube, a traveling-wave tube, a gyrotron, or an all solid-state microwave source. The circulator and water load 12 adopts standard waveguide circulator and water load, so as to protect the microwave as produced. The microwave waveguide resonator 13 can adopts a rectangular conversion waveguide resonator made of materials such as such as aluminum, copper, or stainless steel so as to facilitate the excitation of the microwave plasma, in which though holes matching with the size of the non-metal microwave discharge tube 14 are provided on the upper surface and lower surface of the microwave waveguide resonator 13 where the microwave electric field has a maximum amplitude, and the non-metal microwave discharge tube 14 is in sealed connection with the connection portion of the microwave waveguide resonator 13 via a metal ring. The non-metal microwave discharge tube 14 can be made of various microwave-transmissive and high-temperature-resistant materials such as quartz, ceramic, glass or the like, acting as the discharging area for producing and keeping microwave plasma. In one example, the microwave generator 11 adopts a magnetron, the microwave waveguide resonator 12 adopts a rectangular conversion waveguide resonator made of copper, the non-metal microwave discharge tube 14 adopts a quartz tube having a diameter of 40 mm and is provided at 3.6 cm from the end of the microwave waveguide resonator (calculated by ¼ wavelength of the microwave waveguide, the wavelength of the microwave waveguide in one example being 14.7 cm), and the discharge wire 15 adopts a copper wire.

The non-metal garbage conveyor 20 has a structure shown in FIG. 2, comprising a material conveyor belt 12 with sieve pores and an electric motor 22. In particular, the sieve pores are evenly provided along an axis direction of the material conveyor belt for passing the leachate and molten plastic on the material conveyor belt therethrough, which adopts a conventional stainless steel mesh belt in one example. The electric motor is used for driving the material conveyor belt, and fixed on the side wall of the housing of the gasifier. It can be a conventional motor, being used for adjusting the conveying speed of the material conveyor belt so as to control the time period when the microwave plasma treats the garbage in the gasifier.

The reaction tank 30 has a section having upper near-rectangular shape and lower hopper shape, and is made of a metal material. Pores are provided on two opposite side walls in the middle part of the reaction tank 30 for the material conveyor belt 21 to pass therethrough. In one example, the sewage extrusion separator 40 adopts a conventional extrusion solid-liquid separator.

Other components of the present application are conventional products or can be implemented by the existing technologies in the art. All the equipment in the present application is subject to sealing treatment.

The integrated microwave plasma gasification and recycling system provided by the present application works according to the follow workflow.

(1) Directly discharging initial garbage into the closed chain-plate feeder.

(2) Under the rotary delivery action of the closed chain-plate feeder, the garbage entering the shredder which shreds the initial garbage via shearing, tearing and extruding to reduce the size of the garbage (in particular, the shredded garbage have a particle size of 7-10 cm). In particular, the shredder being a double shaft pulverizer which has strong impact resistance, is capable of breaking metals, and adopts reusable cutters for the purpose of greatly reducing the maintenance cost.

(3) The garbage entering the closed magnetic separator which separates metal materials from the pulverized materials for reuse.

(4) The garbage from which the metal materials are separated entering the metal recovery tank and the remnant non-metal garbage entering the microwave plasma gasifier for being processed.

The non-metal garbage enters the sewage extrusion separator via the feed port of the microwave plasma gasifier, with the leachate produced by the extrusion of the sewage extrusion separator falling into the hopper 50 via the sieve pores in the material conveyor belt and entering the integrated sewage treatment equipment via the leachate recovery port. The solid non-metal garbage produced by the extrusion of the sewage extrusion separator is carried to the microwave plasma torch generation area of the reaction tank 30 via the conveyor belt, so as to be processed by the microwave plasma torch, that is, subject to decomposition and gasification process of the solid non-metal garbage. (a) Regarding the undegradable garbage such as plastics, except for gasified portions (producing CO2, CO, H2, H2O, etc.), most of them will be molten and discharged into the plastic slag recovery tank from the plastic slag recovery port 43 via the sieve pores in the material conveyor belt, in which the molten plastic slag will automatically condense to solid plastic slags due to the temperature difference during the process in which the molten plastic slag enters the plastic slag recovery tank. (b) The remnant solid non-metal garbage (which are mainly organic mass, for example, fruit peels, fruit cores, wood pieces, possibly containing some bricks, tiles, or stones present in the garbage) are carried to the solid remnant recovery port 42 of the gasifier via the material conveyor belt to enter the remnant pulverizer. (c) The gases produced during the gasification (including carbon monoxide, carbon dioxide, hydrogen gas, water vapor, and some minor odorous organic waste gases) enters the odor treatment device via the exhaust port 41.

(5) Post-gasification treatment. (a) The liquid waste discharged from the leachate recovery port 44 of the microwave plasma gasifier are subject to simple settlement via the integrated sewage treatment device for harmless treatment, with the purified water resources thus produced being led to the aerobic fermentation tank for fermenting. (b) The solid remnants discharged via the solid remnant recovery port 42 of the microwave plasma gasifier are pulverized into pieces or masses of 5 cm or smaller by the remnant pulverizer, so as to be reduced in size and then fermented in the aerobic fermentation tank. (c) The gases discharge from the exhaust port 41 of the microwave plasma gasifier is deodorized in the odor treatment device and recovered in the gas recovery tank; and the half products of organic fertilizer produced by the fermentation in the aerobic fermentation tank are subject to sieving in the decompose material forming and sieving machine to remove some bricks, tiles, or stones which are relatively large or missed during the process, so as to provide decomposed materials which is recovered in the decomposed material tank.

Those provided above are merely some preferred embodiments of the present application. It is to be noted that, some improvements and modifications can be made by those skilled in the art without departing from the principle of the present application, and should be considered to fall within the scope of the present application.

What is claimed is:

1. An integrated microwave plasma gasification and recycling system for domestic garbage, characterized in that the system being fixed in a carriage of a garbage truck having a garbage inlet, and comprising a closed chain-plate feeder, a shredder, a closed magnetic separator, a microwave plasma gasifier, an odor treatment device, a remnant pulverizer, an integrated sewage treatment equipment, a decomposed material forming and screening machine, an aerobic fermentation tank, a decomposed material recovery tank, a plastic slag recovery tank, a metal recovery tank, and a gas recovery tank; the closed magnetic separator has a metal material discharge port and a non-metal garbage discharge port, the microwave plasma gasifier has a feed port, a solid remnant recovery port for recovering organic garbage, a plastic slag recovery port, a leachate recovery port and an exhaust port, and the aerobic fermentation tank has a solid garbage feed port, a liquid waste feed port and a discharge port; wherein the garbage inlet of the carriage of the garbage truck is connected with a feed port of the closed chain-plate feeder, and original domestic garbage is charged into the closed chain-plate feeder via the feed port of the closed chain-plate feeder; a discharge port of the closed chain-plate feeder is connected with a feed port of the shredder; a discharge port of the shredder is connected with the feed port of the closed magnetic separator; the non-metal garbage discharge port of the closed magnetic separator is connected with the feed port of the microwave plasma gasifier, and the metal material discharge port of the closed magnetic separator is connected with the metal recovery tank; the solid remnant recovery port, the plastic slag recovery port, the leachate recovery port and the exhaust port of the microwave plasma gasifier are connected with a feed port of the remnant pulverizer, the plastic slag recovery tank, a feed port of the integrated sewage treatment equipment, and a gas inlet of the odor treatment device, respectively, and the gas outlet of the odor treatment device is connected with the gas recovery tank; a discharge port of the remnant pulverizer and a discharge port of the integrated sewage treatment equipment are connected with the solid garbage feed port and liquid waste feed port of the aerobic fermentation tank, respectively; and the discharge port of the aerobic fermentation tank is connected with a feed port of the decomposed material forming and screening machine, and a discharge port of the decomposed material forming and screening machine is connected with the decomposed material recovery tank.

2. The system according to claim 1, characterized in that the microwave plasma gasifier comprises a housing and a microwave plasma torch generator, a non-metal garbage conveyor with sieve pores, a reaction tank, a sewage extrusion separator, and a hopper respectively fixed within the housing via brackets; the exhaust port of the microwave plasma gasifier is provided at a top portion of the housing, the plastic recovery port and the leachate recovery port of the microwave plasma gasifier are respectively provided at a bottom portion of the housing, and the feed port and the solid remnant recovery port of the microwave plasma gasifier are provided at an upper part of two opposite side walls of the housing; wherein the reaction tank is located in a left part of the microwave plasma gasifier, with a top part and a bottom part of the reaction tank being connected with the exhaust port and the leachate recovery port of the microwave plasma gasifier, respectively; the microwave plasma torch generator is disposed close to an upper right part of the reaction tank, and a microwave plasma torch emission end of the microwave plasma torch generator is located within the reaction tank; the non-metal garbage conveyor is located below the microwave plasma torch emission end and extends through a middle part of the reaction tank, with one end thereof disposed closely under the solid remnant recovery port and the other end thereof fixed on the side wall of the housing opposite to the solid remnant recovery port; the sewage extrusion separator and the hopper are located above and under the non-metal garbage conveyor, respectively, and are both co-axially disposed at a right side of the reaction tank, with a feed port of the sewage extrusion separator being connected with the feed port of the microwave plasma gasifier and a bottom of the hopper being connected with the leachate recovery port of the microwave plasma gasifier.

3. The system according to claim 2, characterized in that the microwave plasma torch generator comprises sequentially connected microwave generator, circulator and water load and microwave waveguide resonator; a non-metal microwave discharge tube used for emitting a microwave plasma torch is provided at a position where the microwave waveguide resonator has a maximum amplitude of microwave electric field, the non-metal microwave discharge tube is perpendicular to an axis of the microwave waveguide resonator and has a lower end protruding out of the microwave waveguide resonator, and a discharge wire is further fixed within the non-metal microwave discharge tube.

4. The system according to claim 3, characterized in that the microwave generator is selected from any one of the group consisting of a magnetron, a velocity-modulated tube, a traveling-wave tube, a gyrotron, or an all solid-state microwave source.

5. The system according to claim 3, characterized in that the non-metal microwave discharge tube is made of a microwave-transmissive non-metal material, and the non-metal microwave discharge tube is in sealed connection with a connection portion of the microwave waveguide resonator via a metal ring.

6. The system according to claim 2, characterized in that the non-metal garbage conveyor comprises a material conveyor belt with sieve pores and an electric motor; wherein the sieve pores are evenly provided along an axis direction of the material conveyor belt for passing leachate and molten plastic on the material conveyor belt therethrough.

7. The system according to claim 6, characterized in that pores are provided on two opposite side walls in the middle part of the reaction tank for the material conveyor belt to pass therethrough.

* * * * *